(12) United States Patent
Rochelet et al.

(10) Patent No.: US 11,293,045 B2
(45) Date of Patent: Apr. 5, 2022

(54) METHOD FOR ELECTROCHEMICAL DETECTION OF MYCOBACTERIA

(71) Applicants: UNIVERSITÉ DE BOURGOGNE, Dijon (FR); INSTITUT NATIONAL DE LA RECHERCHE AGRONOMIQUE—INRA, Paris (FR)

(72) Inventors: Murielle Rochelet, Dijon (FR); Élodie Barbier, Rouvres-Sous-Meilly (FR); Alain Hartmann, Dijon (FR)

(73) Assignees: UNIVERSITÉ DE BOURGOGNE, Dijon (FR); INSTITUT NATIONAL DE RECHERCHE POUR LAGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 288 days.

(21) Appl. No.: 16/499,391

(22) PCT Filed: Mar. 29, 2018

(86) PCT No.: PCT/FR2018/050769
§ 371 (c)(1),
(2) Date: Sep. 30, 2019

(87) PCT Pub. No.: WO2018/178578
PCT Pub. Date: Oct. 4, 2018

(65) Prior Publication Data
US 2020/0048678 A1    Feb. 13, 2020

(30) Foreign Application Priority Data
Mar. 31, 2017   (FR) ....................... 1752787

(51) Int. Cl.
*C12Q 1/04* (2006.01)
*C12Q 1/48* (2006.01)
*G01N 27/327* (2006.01)

(52) U.S. Cl.
CPC .............. *C12Q 1/04* (2013.01); *C12Q 1/48* (2013.01); *G01N 27/3275* (2013.01)

(58) Field of Classification Search
None
See application file for complete search history.

(56) References Cited

FOREIGN PATENT DOCUMENTS

WO    WO-2018023134 A1 *  2/2018   ............... C12Q 1/04

OTHER PUBLICATIONS

Backus et al. J. Biol. Chem. (2014) 289 (36): 25041-25053 (Year: 2014).*
Sims et al. Current Drug Metabolism (2008) 9: 510-519 (Year: 2008).*
Boucau J. et al., "A Couple assay measuring Mycobacterium tuberculosis antigen 85C enzymatic activity", Analytical Biochemistry, vol. 385, No. 1, Oct. 21, 2008, pp. 120-127, XP025838523.
International Search Report for corresponding application PCT/FR2018/050769 filed Mar. 29, 2018; Report dated Jun. 25, 2018.
Phunpae Ponrut, et al., "Rapid diagnosis of tuberculosis by identification of Antugen 85 in mycobacterial culture", Diagnostic Microbiology and Infectious Disease, vol. 78, No. 3, Dec. 7, 2013, pp. 242-248, XP028610595.

* cited by examiner

*Primary Examiner* — Susan M Hanley
(74) *Attorney, Agent, or Firm* — Cantor Colburn LLP

(57) ABSTRACT

The present invention relates to a novel process for biological detection of mycobacteria via electrochemical analysis methods of the catalytic activity of antigen 85.

11 Claims, 9 Drawing Sheets

FIGURE 4

METHOD FOR ELECTROCHEMICAL DETECTION OF MYCOBACTERIA

FIELD OF THE INVENTION

The subject of the present invention is a process or a method for detecting mycobacteria, which is based on measuring acyltransferase activity, in particular the catalytic activity of Antigen 85, with an electrochemical analysis method.

The present invention is applicable in human and veterinary medicine, for the diagnostic of human and animal tuberculosis and mycobacteriosis, and also in environmental diagnosis.

In the description below, the references between square brackets ([ ]) refer to the list of references presented at the end of the text.

PRIOR ART

Mycobacteria belong to the phylum Actinobacteria and are characterized by a wall rich in mycolic acids giving them particular staining properties associated with resistance of their wall to successive decolorings by an acid and then by 90° alcohol (AAFB: Acid-Alcohol-Fast Bacilli). Approximately 200 species belonging to the *Mycobacterium* genus have been identified to date.

Among them, mycobacteria referred to as tuberculous are necessary pathogenic bacteria with predominantly respiratory tropism, that are responsible for tuberculosis in human beings and animals. Non-tuberculous mycobacteria (termed atypical or environmental) group together opportunistic bacteria responsible for mycobacteriosis in human beings and animals. Leprosy is also a disease caused by a *Mycobacterium*, *Mycobacterium leprae*.

Human tuberculosis is mainly due to *M. tuberculosis*, but can also be caused by *M. africanum, M. canettii, M. bovis* in particular. Human tuberculosis represents a major health problem worldwide since it is the most deadly infectious disease in the world (approximately 1.5 million deaths in 2013) with HIV (AIDS). The WHO (World Health Organization) estimates the number of new cases to be approximately 9 million each year.

With regard to animals, tuberculosis affects a very large number of species: bovines, members of the goat family and also numerous wild species, such as small rodents, for example.

Atypical mycobacteria, widely found in the environment (soil and water), exhibit a very variable pathogenicity in human beings and animals.

In human beings, the incidence of infections associated with atypical mycobacteria appears to increase in industrialized countries. They generally occur where there is a background of local or general immunodepression causing mainly pulmonary infections (for example *M. avium* and *M. intracellulare, M. xenopi, M. kansasii, M. malmoense*), lymphatic infections (*M. avium* and *intracellulare, M. kansasii, M. scorofulaceum*), skin infections (*M. marinum, M. ulcerans,* M. chelonae), or even systemic infections (*M. avium* and *intracellulare, M. kansasii, M. haemophilum, M. xenopi, M. gevanense*), etc. In animals, some cause contagious infections with high morbidity and mortality (*paratuberculosis* in bovines: *M. avium* ssp. *paratuberculosis* and "tuberculosis" in birds: *M. avium* ssp. *avium* for example). The persistence of atypical mycobacteria in the environment, their resistance to detergents and the ability of certain species to form biofilms, in particular in water networks, may be responsible for the contamination of surface water and water distribution networks responsible for contaminating human beings.

The detection of mycobacteria in human beings, animals or in the environment is based on the following techniques.

The historical detection method is based on a microscopic examination of samples (sputum smear, ground material from lesions, etc.) which makes it possible to demonstrate the presence of acid-alcohol-fast bacilli (AAFBs), a partially specific characteristic of mycobacteria. In human beings, the microscopic examination is carried out on a biological sample smear or the centrifugation pellet obtained after fluidization-decontamination of contaminated pathological products. Two stainings are used: Ziehl-Neelsen staining (conventional microscopy) and auramine staining (fluorescence microscopy). It is a key examination since the majority of cases of tuberculosis in countries where there is a high incidence are diagnosed in this way in peripheral microscopy centers. Microscopic examination also remains the starting point for the diagnosis scheme adopted in diagnostic laboratories in developed countries. Microscopic examination is easy to implement (little material, personnel not highly qualified) with the result being provided rapidly (2 to 3 hours) and at low cost. However, this examination has several drawbacks: operator-dependent implementation, subjective interpretation of the result, lack of sensitivity (detection of 50% to 70% of pulmonary tuberculosis cases), and also a lack of identification of the species involved. The performance levels thereof are even lower in patients infected with HIV and children (specimens with few bacteria).

With regard to the bacteriological detection of tuberculosis and of mycobacteriosis in human beings and animals, and also that of environmental contamination, the reference technique remains culture on a suitable medium (solid: Coletsos, Lowenstein-Jensen, Middlebrook 7H11 or liquid: Middlebrook 7H9) optionally supplemented with antibiotics and antifungals. The culturing of the bacterium starting from sputum, ground tissue matter, other biological samples or environmental specimens is commonly used and has the advantage of being sensitive. Automated liquid culture systems of Bactec MGIT™ (Becton Dickinson) or BacT/Alert® (BioMérieux) type combine incubation and spectroscopic measurement of bacterial growth. However, this method allows only a delayed diagnosis since, from a microbiological and culture point of view, tuberculous mycobacteria and some atypical mycobacteria are slow-growing microorganisms: at least 1 to 6 weeks of incubation at 37° C. are necessary in order to observe growth of the bacterium on the culture media. Whatever the nature of the sample, a prior decontamination treatment optionally combined with fluidization with physicochemical agents (N-acetylcysteine—sodium hydroxide, sodium hypochlorite, acids, detergents) is essential before it is cultured, in order to prevent the development of fast-growing microorganisms, reducing the sensitivity of the method. Following the culture, the identification of the species can be carried out by DNA hybridization techniques optionally coupled with PCR, gene sequencing, genotyping (insertion sequences, spoligotyping, etc.), by identification of biomarkers (analysis of mycolic acids by liquid-phase chromatography, protein profile by MALDI-TOF mass spectrometry for example). However, all these techniques require expensive laboratory equipment and highly qualified staff and are not therefore suitable for outsourced and rapid diagnosis of mycobacterial infections.

Because of their rapidity (result provided during the day), molecular biology methods are also today widely used in diagnostic laboratories both for human beings and for animals and the environment. Based on the specific amplification of target mycobacterial genes, they allow both the detection of the bacterium and its identification, or even its possible resistance to antibiotics (human diagnosis only). However, their use generally requires suitable infrastructure, expensive equipment and also qualified staff (DNA extraction and interpretation of the results). The GeneXpert® technology developed by the Cepheid laboratory for the molecular diagnosis of human tuberculosis limits the drawbacks mentioned above by virtue of the use of an automated device which carries out all the steps without human intervention. The result obtained in 2 hours makes it possible to detect the presence of a tuberculous mycobacterium and also its potential resistance to rifampicin, a frontline antibiotic used in the treatment of human tuberculosis. However, its price constitutes a curb on its generalization in countries with low revenues. Furthermore, this technology does not make it possible to carry out more than about twenty analyses per day.

In animals, the diagnosis of tuberculosis is carried out post-mortem after prophylactic screening or a discovery of lesions in the abattoir. It is carried out on ground material from lesions or from lymph nodes. As in human beings, the samples can be cultured after decontamination and/or can be analyzed by molecular biology methods. The limits of this detection are identical to those mentioned above: delayed production of the result with culture and expensive molecular biology automated devices with qualified staff.

Regarding the detection of mycobacteria in the environment, the search for said mycobacteria is not standardized and no standard is currently available. Culture on a suitable medium after chemical decontamination comes up against the same limits as that of biological samples: slow growth with delayed production of the result and contamination of the culture media by fast-growing bacteria in particular. Molecular biology has made it possible to bypass this culture step, but still does not allow suitable quantification.

With a view to proposing new methods of identifying mycobacteria, the detection of specific antigens, such as Ag MPT64 or those of the Antigen 85 (Ag85) complex have been envisioned. To do this, an immunochromatographic test based on the identification of Ag MPT64 after culture (present in tuberculous mycobacteria, absent in atypical mycobacteria) has been sold (SD Bioline TB Ag MPT64, Standard Diagnostic, Inc.). ELISA assays used for the detection of Ag85 in liquid culture filtrates, serum or in cerebrospinal fluid (Phunpae et al., Diagn. Microbiol. Infect. Dis., 78(3): 242-248, 2014 [1]; Kashyap et al., BMC infectious diseases, 7:74, 2007 [2]; Kashyap et al., Clin Diagn Lab Immunol., 12(6):752-758, 2005 [3]) are described in the literature.

The Antigen 85 (Ag85) complex is composed of three secreted homologous proteins: Antigen 85A (Ag85A), Antigen 85B (Ag85B), and Antigen 85C (85C) which share a high sequence identity (68-79%) in their secreted mature forms. They are mycolyltransferases (enzymes having a molecular weight of approximately 30 000 Da) which are involved specifically in the construction and maintenance of the walls of Corynebacteriales—order to which the *Mycobacterium* genus belongs—by catalyzing the transfer of mycolic acid onto polysaccharide structures (arabinogalactan, trehalose). More generally, Ag85 is an acyltransferase which is not only capable of transferring mycolyl groups, but also other acyl groups.

The detection and the activity of Ag85 being widely studied for the search for and evaluation of new methods of diagnosis and of monitoring of the efficacy of antitubercular chemotherapy treatments (Elamin et al., J Microbiol Methods, 79(3):672-678, 2002 [4]) several spectrophotometric methods (UV-visible, fluorescence, etc.) have been described for the assaying of this protein via the measurement of its acyltransferase activity (Boucau et al., Analytical Biochem., 385: 120-127, 2009 [5]; Favrot et al., J. Biol. Chem., 289(36): 25031-25040, 2014 [6]).

International application WO 2011/030160 [7] describes a method for detecting the presence of mycobacteria in an organism or a biological sample via the demonstration of the catalytic activity of Ag85 during the culture step. To do this, molecular probes consisting of a labelled polysaccharide (trehalose and other saccharide derivatives) (radiotracer, fluorophore, nanoparticles, biotin) have been synthesized and added to the culture medium in order to be incorporated into the bacterial wall during bacterial growth by virtue of the transferase activity of Ag85. At the end of this step, the bacteria are rinsed and isolated from the culture medium and then detected using a suitable technique (scintillation counter, fluorimeter, microscopy, NMR, in vivo imaging techniques, etc.). However, this method, which allows the detection of viable mycobacteria by labeling them, can only be envisaged for the analysis of very contaminated samples (about $10^7$ bacilli·$ml^{-1}$) or after quite a long culture step. Furthermore, several steps of rinsing the bacteria are obligatory in order to remove the excess labeled probe not incorporated. Finally, the detection of the marker is carried out using delicate and expensive laboratory instrumental techniques which require qualified staff to implement them and to interpret the results.

Patent application CN102087283 [8] describes a method of electrochemical detection of *M. tuberculosis* using an enzymatic immunosensor based on a solution of chitosan, gold nanoparticles and an antibody specific for the *M. tuberculosis* cell wall. The quantitative measurement is carried out by comparing the signal of the product generated by alkaline phosphatase in the presence of α-naphthyl phosphate before and after incubation with the sample. However, although this method has been applied to the detection of *M. tuberculosis* in milk samples, its use in routine diagnosis cannot be envisaged. This is because the use of vitreous carbon electrodes for the construction of the immunosensor is very restrictive: polishing of the surface and cleaning in a piranha mixture (sulfuric acid and hydrogen peroxide) before each new use. Furthermore, the preparation of the sensitive surface of the immunosensor requires several steps: 1) electrodeposition of a solution containing gold nanoparticles, chitosan and a goat anti-mouse antibody labeled with an alkaline phosphatase, then 2) incubation of a solution of anti-*M. tuberculosis* antibody produced in mice. Finally, once constructed, the immunosensor must be stored at 4° C.

There is thus a need for a method for detecting mycobacteria that is simple and rapid to carry out and that overcomes the drawbacks of the processes of the prior art.

DESCRIPTION OF THE INVENTION

In order to meet this need for a more effective diagnostic test for human, animal and/or environmental tuberculosis for which at the current time there is no suitable solution, the inventors have developed a new electrochemical method capable of rapidly detecting (obtaining the results in approximately 2 to 5 h) the presence or absence of mycobacteria in samples such as, for example, in a culture medium and in human respiratory specimens: the EDMYC (Electrochemical Detection of MYCobacteria) method.

Thus, the inventors have developed a new method for electrochemical detection of mycobacteria via the electrochemical measurement of the acyltransferase activity in the mycobacteria, in particular of the catalytic activity of Ag85 in the presence of a substrate of the enzyme, e.g. p-aminophenyl -6-O-octanoyl-β-D-glucopyranoside (p-AP-OG), and of a cofactor or co-substrate, e.g. trehalose. Indeed, since Ag85 is very widely excreted by mycobacteria, e.g. by *Mycobacterium tuberculosis* and *Mycobacterium bovis*, in liquid culture media, the detection of the acyltransferase activity, in particular of the catalytic activity of Ag85, in the culture medium makes it possible to demonstrate the presence of mycobacteria.

The principle of the invention is based on the fact that acyltransferases such as Ag85 hydrolyze the ester bond of the substrate, and transfer the acyl group thus released onto the cofactor. The product is then detected by voltammetry. According to one particular embodiment, the present invention is based on the capacity of acyltransferases, in particular of Ag85, to hydrolyze the ester bond of p-AP-OG and to transfer the octanoyl group of p-AP-OG onto a sugar, e.g. trehalose, according to a ping-pong mechanism, in order, respectively, to generate p-aminophenyl-β-D-glucopyranoside (p-AP-G) and to form acyltrehalose (FIG. 1). The difference between the potentials of the oxidation peaks of p-AP-OG and of p-AP-G that is observed on the voltammograms (FIG. 2), which is explained respectively by the presence or the absence of the octanoyl group on the molecule, thus makes possible the specific detection of the acyltransferase activity, in particular of the catalytic activity of Ag85, in the presence of p-AP-OG. The intensity of the p-AP-G oxidation peak, chosen as analytic response, is proportional to the amount of acyltransferases, in particular of Ag85, and thus to that of the mycobacteria present in the sample analyzed.

Thus, the inventors have developed a simple and rapid method for detecting mycobacteria and their viability with or without a prior culture step.

To date, the proof of concept of the method has been successfully demonstrated with the detection of several mycobacterial species frequently encountered in pulmonary infections, including *M. tuberculosis*—the principal agent of tuberculosis in human beings—in liquid and solid cultures. The method has numerous advantages compared with microscopic examination, such as the simplicity of its implementation or else an easy interpretation of the results (numerical measurement) with a small, portable and inexpensive piece of equipment. In addition, compared with optical methods, the electrochemical technique proves to be particularly advantageous since it allows the analysis of cloudy or colored samples, with the possibility of offering a quantified measurement, with good sensitivity, by means of single-use screen-printed sensors. Thus, it perfectly satisfies the specifications imposed by the WHO for a test capable for example of replacing the microscopic examination of sputum smears.

In addition, the inventors have demonstrated an improvement in the specificity of the detection method with respect to mycobacteria and Ag85 by proposing 1) the use of a substrate of the enzyme with acyl groups having carbon chains longer than that of p-AP-OG, for example alkyl chains ranging from $C_7H_{15}$ to $C_{29}H_{59}$, and/or 2) a method for extracting and decontaminating actual samples in order to isolate the mycobacteria.

A subject of the present invention is thus a process for electrochemical detection of mycobacteria in a biological sample, said process comprising the steps of:
  a) selecting a substrate of at least one acyltransferase and its cofactor;
  b) bringing said biological sample into contact with said substrate and cofactor;
  c) electrochemically detecting the product resulting from the catalytic activity of said at least one acyltransferase.

According to one particular embodiment of the detection process of the present invention, the biological sample is chosen from the group consisting of: bacterial cultures, biological specimens of human or animal origin, environmental samples, etc. A bacterial culture may for example be obtained on a nutritive agar or in a liquid culture medium, according to techniques well known to those skilled in the art. A biological specimen of human origin may for example be a sample of pulmonary origin (sputum, bronchial secretions, biopsy), a blood sample, a cerebrospinal fluid sample, a urine sample, a sample of intestinal origin (intestinal biopsy, feces), and also any other tissue sample. A biological specimen of animal origin may for example be a tissue sample (lymph node, lung, liver, spleen, etc.), a sample of feces or a milk sample. A sample of environmental origin may for example be a sample of waste water, or of hospital waste water, a sample of treated waste water, a sample of sludge resulting from the treatment of waste water or a soil sample.

According to one particular embodiment of the detection process of the present invention, the acyltransferase substrate is chosen from the group consisting of: p-aminophenyl-6-O-octanoyl-β-D-glucopyranoside, and substrates with acyl groups having alkyl chains ranging from $C_7H_{15}$ to $C_{29}H_{59}$.

According to one particular embodiment of the detection process of the present invention, the cofactor is a sugar chosen from the group consisting of: trehalose, D-glucose.

Preferably, the substrate is p-aminophenyl-6-O-octanoyl-β-D-glucopyranoside, and the cofactor is trehalose. The product formed after enzymatic hydrolysis by the acyltransferases, in particular by Ag85, is p-aminophenyl-β-D-glucopyranoside.

According to one particular embodiment of the detection process of the present invention, the electrochemical detection step c) is carried out by means of an amperometric sensor, which is optionally chemically modified (e.g. with carbon nanotubes, graphene). Preferably, said sensor is a screen-printed sensor, which is preferentially single-use.

In accordance with the invention, an electrochemical analysis means for carrying out the invention can be a potentiometric measurement, an impedance measurement, a coulometric measurement or an amperometric measurement.

According to one advantageous embodiment of the detection process of the present invention, the electrochemical analysis is carried out by an amperometric measurement.

For the purposes of the present invention, the term "amperometric measurement" is intended to mean a measurement of the electric current as a function of a potential difference established between the working electrode and the reference electrode.

The measurement of the electric current can be carried out by means of known amperometric techniques, preferentially by potential sweep voltammetry which may be linear, cyclic, or pulse voltammetry or else of the potential step type, such as chronoamperometry.

In one particularly advantageous embodiment of the detection process of the present invention, the presence of p-aminophenyl-β-D-glucopyranoside is measured by cyclic or linear voltammetry.

The use of these techniques requires an assembly which may be a two-electrode or even three-electrode assembly, that is to say an assembly comprising a working electrode, a reference electrode and optionally an auxiliary electrode (counter electrode). The working electrode, the surface of which serves as a site for electron transfer, can be based on carbon or based on a noble metal or else based on metal oxide. The reference electrode is an electrode of which the potential is constant, which makes it possible to impose a precisely defined potential on the working electrode. The reference electrode may be an Ag/AgCl electrode. The counter electrode, which makes it possible to establish the passage of the electric current with the working electrode, can be fabricated with an inert material, such as platinum or carbon. Those skilled in the art will know how to choose and combine the appropriate electrodes according to their general knowledge.

With regard to the method of manufacturing the electrodes, the screen-printing technique is preferable, although other methods of industrial fabrication, such as rotagravure, inkjet printing, 3D printing or optionally photolithography, can be envisioned. Electrodes obtained by screenprinting are particularly well suited because they can be produced in bulk at low cost, and thus can optionally be single-use. Furthermore, their geometric shape and also their size can be easily modulated. These electrodes can be screenprinted in the form of a sensor and optionally integrated into the bottom of the wells of a microplate or of other supports or systems allowing the filtration of the bacterial suspensions and the incubation of p-aminophenyl-6-O-octanoyl-β-D-glucopyranoside and of trehalose.

According to one particular embodiment of the detection process of the present invention, the amperometric measurement is carried out with a screen-printed sensor. It makes it possible to perform the measurement in a small volume of solution of about a few microliters.

According to one particular embodiment of the detection process of the present invention, the amperometric measurement is carried out with a device involved three electrodes: an Ag/AgCl reference electrode, a carbon working electrode and a carbon counter electrode.

According to another particular embodiment of the detection process of the present invention, the amperometric measurement is carried out with a screen-printed sensor comprising an Ag/AgCl reference electrode, a carbon working electrode and a carbon counter electrode.

The presence of p-aminophenyl-β-D-glucopyranoside is indicated by the presence of an anodic oxidation current in an interval of potentials and the absence of said current for a control devoid of hydrolyzed p-aminophenyl-6-O-octanoyl-β-D-glucopyranoside.

When the p-aminophenyl-β-D-glucopyranoside is subjected to a measurement by cyclic voltammetry, its presence is indicated by an anodic oxidation current peak specific to p-aminophenyl-β-D-glucopyranoside in a determined interval of potentials (+0.3 to +0.5 V vs. Ag/AgCl).

Preferably, the biological sample to be tested is prepared so as to isolate the mycobacteria that it contains while at the same time eliminating a maximum amount of contaminants before the contacting and detection steps. To do this, an extraction step with an apolar solvent such as, for example, hexane is necessary in order to selectively isolate the mycobacteria—the wall of which is very hydrophobic—from the sample previously placed in solution in a fluidizing agent such as N-acetylcysteine for a respiratory specimen or in a phosphate buffer with a neutral pH for a soil sample, for example. In the case of complex samples such as soil, where millions of different bacterial species can coexist, the extraction step can be followed by a decontamination of the extract with, for example, an acid (HCl, $H_2SO_4$) and/or a base (NaOH) or a quaternary ammonium.

Thus, a subject of the present invention is also a process for isolating mycobacteria from a biological sample, said process comprising the steps of:
 a) placing said biological sample in solution;
 b) treating with an apolar solvent the solution obtained in step a); and
 c) recovering the mycobacteria by filtration or centrifugation of the solution resulting from step b); and
 d) recovering the mycobacteria from the filtrate or from the centrifugation pellet obtained at the end of step c).

According to one particular embodiment of the process for isolating mycobacteria of the present invention, the extraction step b) is carried out with a solution of hexane or a hexane-isopropanol mixture.

According to one particular embodiment of the process for isolating mycobacteria of the present invention, the process can also comprise a step of decontaminating a') the biological sample placed in solution at the end of step a) and before step b), and/or a step of decontaminating c') the filtering membrane at the end of step c) and before step d), with acidic solutions (e.g. solution of hydrochloric acid) and/or basic solutions (e.g. solution of sodium hydroxide or of quaternary ammonium), and/or addition of sodium hypochlorite, and/or with at least one other disinfecting compound (e.g. chlorhexidine or squalamine).

According to one particular embodiment of the process for isolating mycobacteria of the present invention, step c') can be followed, before step d), by a rinsing step c"), for example in the presence of phosphate buffer, in order to remove the sodium hypochlorite (bleach) from the filter (preferably made of Teflon).

According to one particular embodiment of the process for isolating mycobacteria of the present invention, step d) of recovering the mycobacteria is carried out by scraping the filter with a loop (wire loop) in order to detach the cells from the filter. The mycobacteria thus recovered are then cultured in a suitable medium (enriched and supplemented medium 7H11), for approximately two months, at 37° C., in order to allow counting thereof.

A subject of the present invention is also a kit for carrying out the process for electrochemical detection of mycobacteria in a biological sample according to the present invention, said kit comprising:
 a) a device and the reagents for collecting and preparing the biological sample to be tested;
 b) a device comprising a substrate of Ag85 and its cofactor for the incubation with Ag85;
 c) a device for the electrochemical detection by means of a suitable reader.

For the purposes of the present invention, the term "device" of step a) is intended to mean a sealed container, which is preferably single-use, for example a single-use tube or column equipped with a filtration system in which the steps of diluting the sample, extracting, decontaminating if necessary and recovering the mycobacteria are carried out.

For the purposes of the present invention, the term "device" of step b) is intended to mean a sealed container, which is preferably single-use, for example a single-use tube equipped with a filtration system in which the incubation of the mycobacteria with the substrate and the co-substrate is carried out.

For the purposes of the present invention, the expression "device for the electrochemical detection" of step c) is intended to mean for example an amperometric sensor, which is preferably screenprinted and single-use, for example those sold by the companies Dropsens and Palmsens. The amperometric sensor can optionally be integrated into the device of step b.

By way of example of a suitable reader, mention may be made of portable readers based on the principle of the blood glucose reader, for example those sold by the companies Dropsens and Palmsens and which make it possible to carry out the measurements in a few seconds.

BRIEF DESCRIPTION OF THE FIGURES

FIG. 4 represent the steps carried out during the detection of Ag85 in the supernatant of a culture of mycobacteria.

EXAMPLES

Figure 1:
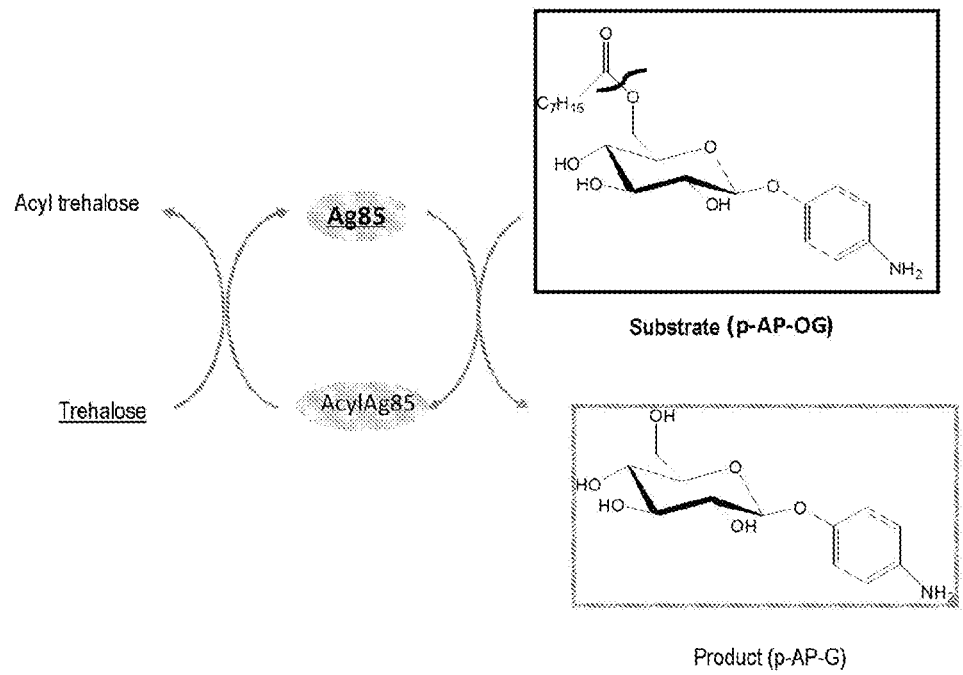
FIG. 1 represents the scheme of the principle of the enzymatic reaction catalyzed by Ag85 with p-AP-OG and trehalose as substrate and substrate, respectively.
Figure 2:
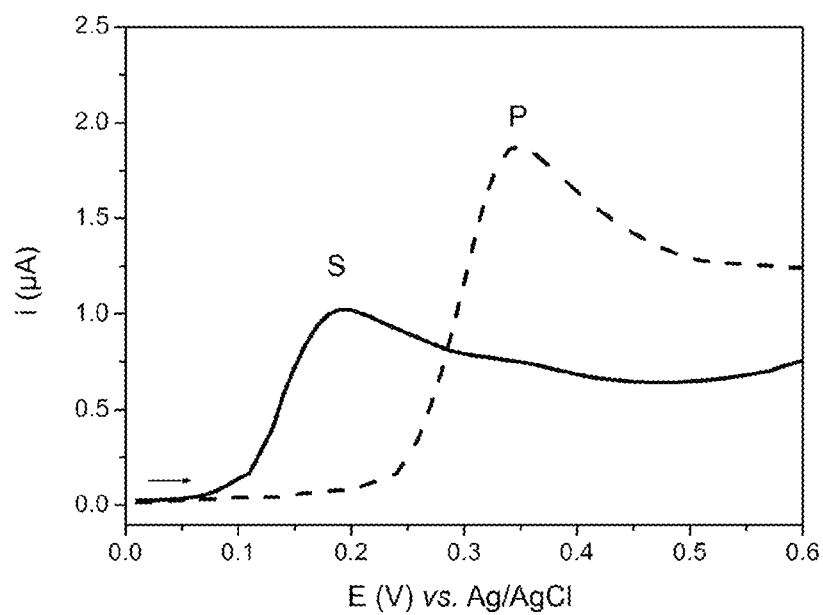
FIG. 2 represents the linear voltammograms (v=50 mV·s$^{-1}$) of a solution of substrate (p-AP-OG; S) and of product (p-AP-G; dashed curve; P) at $5 \times 10^{-4}$ M in PBS (pH 7.5)—0.2% DMSO.

Example 1: Materials and Methods 1.1. Reagents and solutions

- the p-aminophenyl-6-O-octanoyl-β-D-glucopyranoside ($C_{20}H_{31}NO_7$; p-AP-OG) and also the p-aminophenyl-6-β-D-glucopyranoside ($C_{12}H_{17}NO_6$; p-AP-G) were synthesized at the Institut de Chimie Moléculaire (Molecular Chemistry Institute) of the Universite de Bourgogne.
- the trehalose and the dimethyl sulfoxide (DMSO) were supplied by Sigma-Aldrich.
- the *Mycobacterium tuberculosis* Ag85B (Ag 85; ab73632) was purchased from Abcam and reconstituted according to the supplier's recommendations.
- the hexane and the isopropanol come from the Carl Roth laboratory.
- the phosphate buffer (16.7 mM $NaH_2PO_4 \cdot 2H_2O$; 33.3 mM $Na_2HPO_4 \cdot 12H_2O$ pH 7.5, 50 mM) was prepared with Milli-Q 18 MΩ water (Millipore System).
- the liquid medium (Middlebrook 7H9 Broth Base, Fluka) and solid medium (Middlebrook 7H11 Agar Base, Fluka) and also the constituents of the enrichment product (oleic acid, bovine albumin, dextrose and catalase) were supplied by Sigma-Aldrich. The tryptone (casein peptone) was supplied by VWR. The heat-inactivated bovine serum was supplied by Dutscher.
- the BD BACTEC™ MGIT™ liquid medium tubes (mycobacterial growth indicator tubes) were supplied by Becton Dickinson, as were the BACTEC™ MGIT™ growth supplement and the lyophilized BBL MGIT™ PANTA antibiotic complex. The medium was prepared according to the distributor's recommendations.

1.2. Strains and Culture Media

- the strains of *Mycobacterium intracellulare, M. avium* ssp. *avium, M. bovis* BCG strain Pasteur (avirulent vaccine strain) and *M. xenopi* were supplied by the Laboratoire National de Référence [French National Reference Laboratory] for bovine tuberculosis of Maisons-Alfort. The strain *M. avium* ssp. *paratuberculosis* K10 was supplied by the INRA [French National Institute for Agronomic Research] of Tours. These strains were handled in an L2 containment laboratory.
- the strain of *M. tuberculosis* H37Rv originates from the Laboratory associated with the Centre National de Référence des Mycobacteries et de la Résistance des Mycobacteries aux Antituberculeux [French National Reference Center for mycobacteria and the resistance of mycobacteria to anti-tuberculosis agents] (Hopitaux Universitaires [University hospitals] St Louis—Lariboisiere—F. Widal). Since the *M. tuberculosis* strains belong to "Class 3" infectious risks category, all the experiments with the strain *M. tuberculosis* H37Rv were carried out in an L3 laboratory.
- the strains of *Staphylococcus aureus* (DMSZ20231), *Staphylococcus epidermidis* (DSMZ20044),

*Pseudomonas monteilii* (DMSZ14164), *Enterococcus faecalis* (DMSZ20478), *Enterococcus faecium* (DMSZ20477), *Escherichia coli* (DMSZ30083). and *Stenotrophomonas maltophilia* (DMSZ50170) were ordered from the Leibniz Institute DSMZ-German Collection of Microorganisms and Cell Cultures.

the strains of *Streptococcus pyogenes*, *Pseudomonas aeruginosa*, *Pseudomonas fluorescens*, *Rhodococcus corallinus*, *Achromobacter xylosoxidans*, *Citrobacter freundii*, *Enterobacter cloacae* and *Klebsiella pneumoniae* were kindly supplied by the INRA and the CHU [University hospital center] of Dijon.

the liquid culture medium was prepared by diluting 5.9 g of Middlebrook 7H9 Broth Base and 1.25 g of tryptone in 1 l of milli-Q water, then autoclaved for 15 minutes at 121 degrees.

the solid culture medium was prepared by diluting 18.9 g of Middlebrook 7H11 Agar Base in 800 ml of milli-Q water, then autoclaved for 15 minutes at 121 degrees.

With the aim of promoting the growth of the mycobacteria, the liquid and solid culture media were enriched with 10% of a mixture consisting of oleic acid, albumin, dextrose and catalase (OADC; Table 1). The 7H11 medium was also supplemented with 10% of heat-inactivated bovine serum.

Oleic acid and long-chain fatty acids are essential for mycobacteria metabolism. Dextrose is an energy source. Catalase allows neutralization of peroxides, which can be toxic to bacteria. Albumin plays a protective role against toxic agents.

TABLE 1

Composition of the OADC enrichment

| Components | |
|---|---|
| Dextrose | 20.0 g |
| Bovine albumin | 50.0 g |
| Oleic acid* | 0.6 |
| Catalase* | 0.003 g |
| Water | 1 l |

1.3. Sensors and Measurement Apparatus

The electrochemical measurements were carried out by linear voltammetry (v=50 mV·s$^{-1}$) with a 910 PSTAT mini potentiostat (Metrohm, France) powered through the USB connection of the computer and controlled by the PSTAT software (version 1.0). To do this, drops of solution of 30-50 µl were deposited on the surface of single-use screen-printed carbon sensors supplied by Dropsens (DRP-110) and connected to the potentiostat via the connector (DRP-DSC). The amperometric detection of the product generated during the reaction catalyzed by Ag85 was always carried out after a step of filtration of the reaction mixture with a filtration device (Microcon 10 kDa, Millipore). All the potentials are measured relative to the Ag/AgCl reference electrode.

Figure 4:
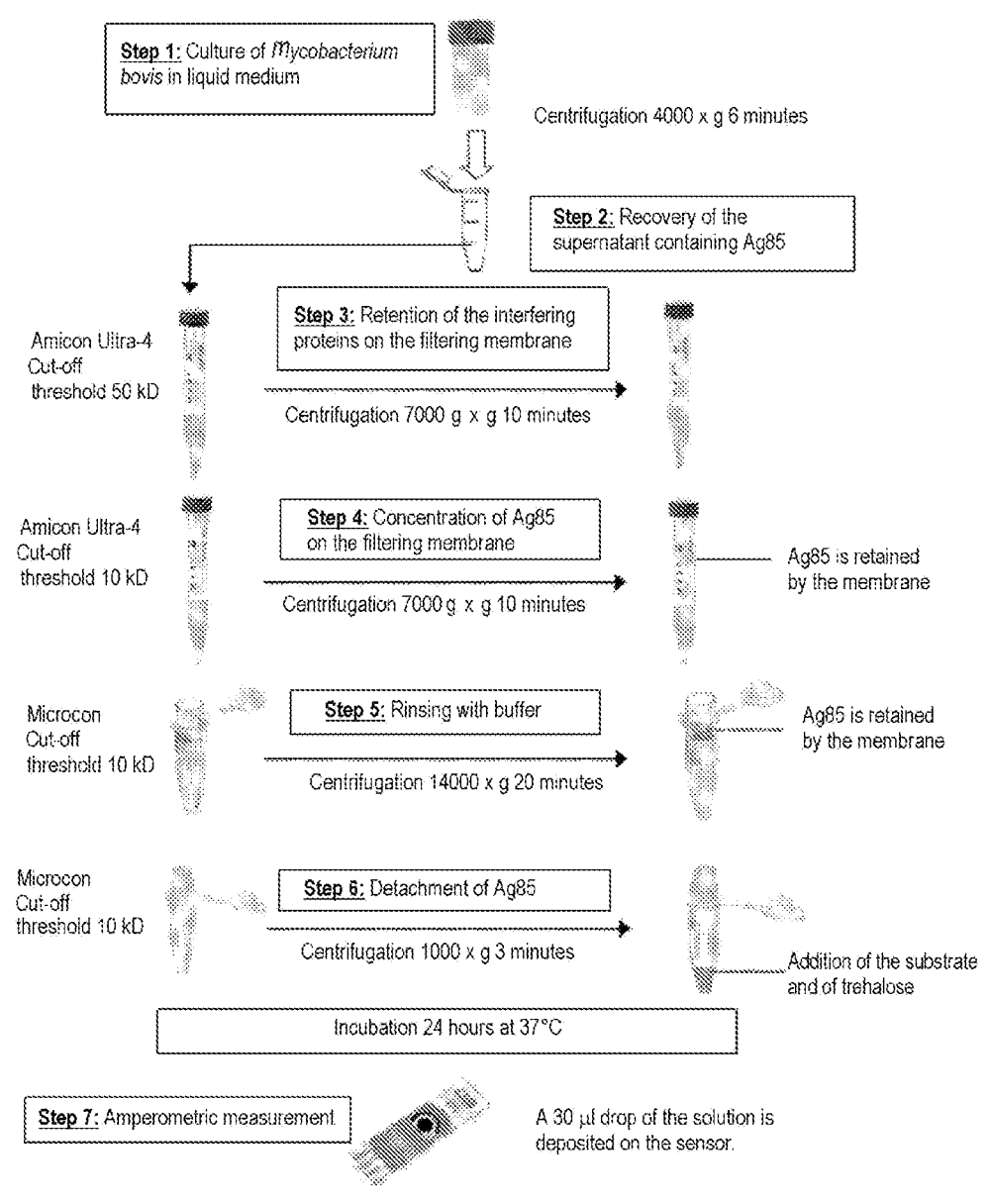

1.4. Detection of Ag85 in the Supernatant of a Liquid Culture of *M. bovis* BCG The principle of this 7-step protocol is shown schematically in FIG. 4. 4 ml of three-week-old culture of *M. bovis* BCG were centrifuged at 4 000×g for 6 min (step 1). The supernatant was recovered (step 2) and deposited in the reservoir of a filtration device (Amicon® Ultra 4 ml (porosity of 50 kD allowing the Ag85 Complex to pass through, Merck Millipore, France)) in order to remove the interfering proteins from the culture medium, in particular the BSA and catalase, and centrifuged for 10 min at 7 000×g (step 3). The filtrate is deposited in the reservoir of a second Amicon® Ultra 4 ml with a porosity of 10 kD, allowing the concentration of the Ag85 Complex after centrifugation for 10 min at 7 000×g. The filtering membrane is rinsed with 500 µl of PBS and centrifuged according to the same parameters as previously (step 4). The volume retained by the membrane (200-250 µl) is then deposited in a Microcon® device with a porosity of 10 kD, centrifuged for 20 min at 14 000×g and then rinsed with PBS (step 5). The filtration device is turned upside down and centrifuged for 3 min at 1 000×g in order to detach the Ag85 Complex (final volume of approximately 80 µl) (step 6). 10 µl of a solution of trehalose at $5\times10^{-3}$ M in PBS and 10 µl of a solution of p-AP-OG at $2\times10^{-3}$M in PBS are finally added to the filtrate. After incubation at 37° C. for 24 h, the reaction medium is filtered on a Microcon® device with a porosity of 10 kD (15 min. at 14 000×g) and then 30 µl of filtrate are deposited on the sensor and analyzed by voltammetry (step 7).

1.5. Detection of Ag85 in the Bacterial Pellet Obtained from the Liquid Cultures of *M. intracellulare, M. Avium* and *M. Xenopi*

Volumes of 1 ml of liquid culture of each mycobacterial species (~$10^6$ bacilli·$ml^{-1}$) were centrifuged at 6 000×g for 6 minutes. Once the supernatant had been removed, the bacterial pellets were rinsed with 1 ml of PBS and then centrifuged at 6 000×g for 6 minutes. After removal of the supernatant, 10 µl of p-AP-OG at $2\times10^{-3}$ M, and 10 µl of trehalose at $5\times10^{-3}$ M are added to the bacterial pellets. After a step of incubation for 4 hours at 37° C. with shaking, the electrochemical measurement of the product of the enzymatic reaction was carried out according to the protocol described in section 1.3.

A negative control (enriched 7H9 medium without bacteria) was analyzed in duplicate in the same way.

1.6. Detection of Ag85 in *M. tuberculosis*

1.6.1. The Liquid Culture

Two samples of 7.5 ml of liquid culture of *M. tuberculosis* (~$10^7$ bacilli·$ml^{-1}$) were centrifuged at 7 000×g for 10 minutes. In order to separately analyze the bacterial pellet and the supernatant, the latter was transferred into sterile tubes.

Analysis of the Bacterial Pellet:

Each bacterial pellet was rinsed by adding 100 µl of PBS, then the liquid was removed by turning the tube upside down on an absorbent paper (Whatman). 20 µl of p-AP-OG at $2\times10^{-3}$ M and 20 µl of trehalose at $5\times10^{-3}$M were added to the tubes and incubated for 4 hours at 37° C. without shaking. Negative controls (PBS) were analyzed in duplicate in the same way. The electrochemical measurement of the product of the enzymatic reaction was carried out according to the protocol described in section 1.3.

Analysis of the Supernatant:

Six ml of each culture supernatant were centrifuged at 7 000×g for 20 min in an Amicon 50 kDa filtration device (Millipore). The filtered liquid was transferred into an Amicon 10 kDa filtration device and then centrifuged at 7 000×g for 20 min. The filter was then rinsed with 1 ml of PBS and then centrifuged at 7 000×g for 20 min. The volume of residual liquid remaining on the filter was transferred into a tube to which 30 µl of p-AP-OG at $2\times10^{-3}$ M and 30 µl of trehalose at $5\times10^{-3}$ M were added. The reaction mixture was incubated for 4 hours at 37° C. without shaking. A negative control (enriched 7H9 medium without bacteria) was analyzed in duplicate in the same way. The electrochemical measurement of the product of the enzymatic reaction was carried out according to the protocol described in section 1.3.

1.6.2. The Isolated Colonies

A few colonies taken from a 7H11 agar were deposited in a 2 ml tube. The colonies were rinsed with PBS, the tubes were centrifuged and the supernatant was removed. 20 µl of p-AP-OG at $2\times10^{-3}$ M and 20 µl of trehalose at $5\times10^{-3}$ M were added to the tubes and incubated for 4 hours at 37° C. without shaking. A negative control (PBS) was analyzed in duplicate in the same way. The electrochemical measurement of the product of the enzymatic reaction was carried out according to the protocol described in section 1.3.

1.7. Extraction and Detection of M. intracellulare in a Sample of Respiratory Origin Respiratory specimens (sputum, tracheal aspiration and bronchial aspiration products) from nontuberculous patients were supplied by the CHU [University hospital center] of Dijon. The samples were fluidized beforehand by the CHU of Dijon with the Digest-EUR kit (Eurobio).

Volumes of 1 ml of respiratory sample were dispensed into sterile 15 ml tubes and then incubated with 200 µl of a liquid culture of M. intracellulare containing $10^6$ bacilli or 200 µl of sterile liquid medium (negative control) overnight at 37° C.

Extraction of M. intracellulare 9 ml of hexane-isopropanol mixture (3:2, v/v) were added to each respiratory specimen tube and stirred for 1 minute. After a centrifugation step at 3 000×g for 2 minutes, the supernatant (that is to say the hexane, and the interface) was removed and then vacuum-filtered on a membrane (Durapore, 25 mm; 0.45 µM). Once rinsed with PBS, the membrane was placed in a small polyethylene bag with welded zip closure having the dimensions of the membrane.

Electrochemical Detection of M. intracellulare in the Extract

A volume of 100 µl of the mixture of substrate at $2\times10^{-3}$ M and trehalose at $5\times10^{-3}$ M, prepared in PBS, was introduced into the bag before it was closed. After an incubation step at 37° C. for 4 hours, the electrochemical measurement of the product of the enzymatic reaction was carried out according to the protocol described in section 1.3.

1.8. Extraction and Detection of M. bovis BCG in a Soil Sample

Extraction of *M. bovis* BCG

The soil microcosms were prepared from a clay-loam soil with pH 7.75, autoclaved twice for 15 min at 121° C. with an interval of 48 h, in order to get rid of the endogenous microflora. Microcosms of 5 g of sterile soil were prepared in 45 ml Falcon tubes, then inoculated with *M. bovis* BCG ($2.6\times10^6$ cfu). After incubation for 12 h at ambient temperature in the dark, each microcosm was subjected to the following extraction protocol. A volume of 15 ml of 0.1 M phosphate buffer was added to each microcosm, then the soil was resuspended by stirring for 2 min in a vortex. Next, a volume of 10 ml of hexane was added to the soil suspension in order to selectively extract the soil microorganisms having a hydrophobic envelope. This mixture was stirred for 15 min on a rotary stirrer. Each tube was centrifuged for 10 min at 4 000×g (swinging bucket rotor, Beckman GS-15R centrifuge) in order to separate the various liquid phases and to sediment the soil particles at the bottom of the tube. The interface containing the targeted microorganisms is located between the aqueous phase and the organic phase. It was removed with a pipette and a 1 ml tip, the end of which was cut off, and then deposited on a 2.5 cm Teflon filtering membrane with a porosity of 0.45 µM (Durapore, Millipore, France). The membrane was subjected to vacuum-suction filtration in order to remove the liquid phase and to concentrate the bacteria on the membrane. Said membrane was placed in a pill bottle containing 1 ml of phosphate buffer for the decontamination step.

Decontamination of the Extract and Counting

This step is very useful, or even essential, for removing the interfering edaphic microbial flora from the soil. To do this, the decontamination protocol combined an acid decontamination (addition of 100 µl of 4% hydrochloric acid, incubation for 20 min) with an estimated pH of 1.3 and a basic decontamination (addition of 200 µl of 4% sodium hydroxide, incubation for 20 min) with an estimated pH of 12.6, then the mixture was neutralized by adding 100 µl of hydrochloric acid before the addition of 1 ml of mixture of sodium hypochlorite and sodium hydroxide. After incubation for 15 minutes, the supernatant was removed, deposited on a new Teflon filtering membrane and rinsed with 20 ml of 0.1 M phosphate buffer in order to remove the bleach. The membrane was then placed in a new pill bottle containing 1 ml of enriched 7H9 and scraped with a loop (wire loop) in order to detach the cells from the filter. For the purpose of counting the mycobacteria extracted, 100 µl of each final suspension were inoculated in triplicate on enriched and supplemented 7H11, and incubated for two months at 37° C.

Example 2: Results 2.1. Voltammetric Behavior of p-AP-OG and of p-AP-G

The voltammograms presented in FIG. 2 show that it is possible to distinguish the voltammetric response of the p-AP-OG substrate (S) from that of the p-AP-G product (P). Indeed, the oxidation peaks detected at potentials of ~+0.2 V and ~+0.4 V (vs. Ag/AgCl) were respectively recorded for p-AP-OG and p-AP-G. This peak potential difference, linked to the presence or absence of the octanoyl electron-withdrawing group, indicates that p-AP-OG can be used as a substrate for the amperometric detection of the acyltransferase activity of Ag85.

Indeed, as shown by the scheme in FIG. 1, Ag85 is capable of hydrolyzing the ester bond of p-AP-OG and of transferring the octanoyl group onto trehalose in order, respectively, to generate p-AP-G and acyl trehalose according to a ping-pong mechanism. Thus, the intensity of the p-AP-G oxidation peak measured at around ~+0.4 V vs. Ag/AgCl can be chosen as an analytic response since its value is proportional to the amount of p-AP-G produced, and thus to that of Ag85, and indirectly to that of the mycobacteria present in the sample to be analyzed.

2.2. Electrochemical Detection of the Acyltransferase Activity of the Ag85 Protein In order to demonstrate the acyltransferase activity of Ag85 in the presence of p-AP-OG and of an acyl group accepter, the reaction mixture containing the Ag85 protein, p-AP-OG and trehalose was incubated in the presence and absence of p-AP-G with stirring for 4 hours at 37° C. A negative control containing only p-AP-OG was analyzed in parallel under the same conditions.

As shown by the series of voltammograms presented in FIG. 3, the curve recorded for the negative control (curve as a line ---) presents one p-AP-OG oxidation peak potential around ~+0.2 V vs. Ag/AgCl, whereas the voltammetric response obtained in the presence of Ag85 (curve as a continuous line) possesses two oxidation peaks located at around +~0.4 and 0.55 V vs. Ag/AgCl, respectively.

A supplementary study (results not presented) showed that the value of the p-AP-OG oxidation peak potential increases as a function of the chloride ion concentration in the solution. Moreover, the information regarding the commercially available Ag85 indicates that the protein was lyophilized from a buffer containing 0.1 M NaCl. Thus, the higher values of the oxidation peak potentials of p-AP-OG and of p-AP-G recorded in the presence of Ag85 are probably due to that of the chlorides in the solution.

Figure 3:
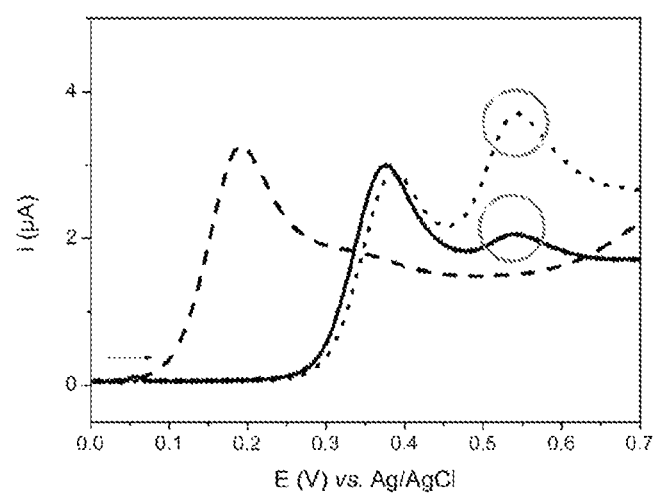
FIG. 3 represent the linear voltammograms (v=50 mV·s$^{-1}$) recorded for a solution of Ag85 (16 ρg·ml$^{-1}$) incubated for 4 h at 37° C. with p-AP-OG ($2 \times 10^{-4}$ M) and trehalose (10 mM) in PBS in the presence (dotted curve) and in the presence (curve as a continuous line) of p-AP-G ($10^{-4}$ M). The curve as a line --- corresponds to the voltammogram obtained after incubation under the same conditions of a solution of p-AP-OG ($2 \times 10^{-4}$ M) in PBS. Reaction volumes=15 µl.
Figure 5:
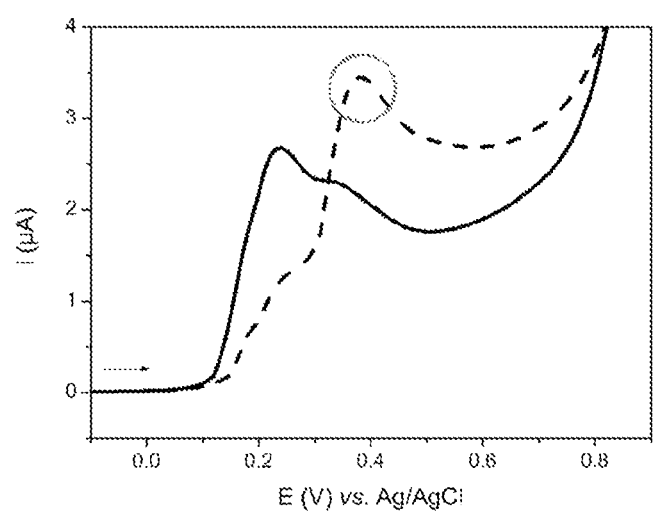
FIG. 5 represents the linear voltammograms (v=50 mV·s$^{-1}$) recorded after carrying out the protocol of FIG. 4 for the analysis of 5 ml of 7H9 medium (curve as a continuous line) and 5 ml of *M. bovis* BCG culture ($1.1 \times 10^7$ cfu·ml$^{-1}$).
Figure 6:
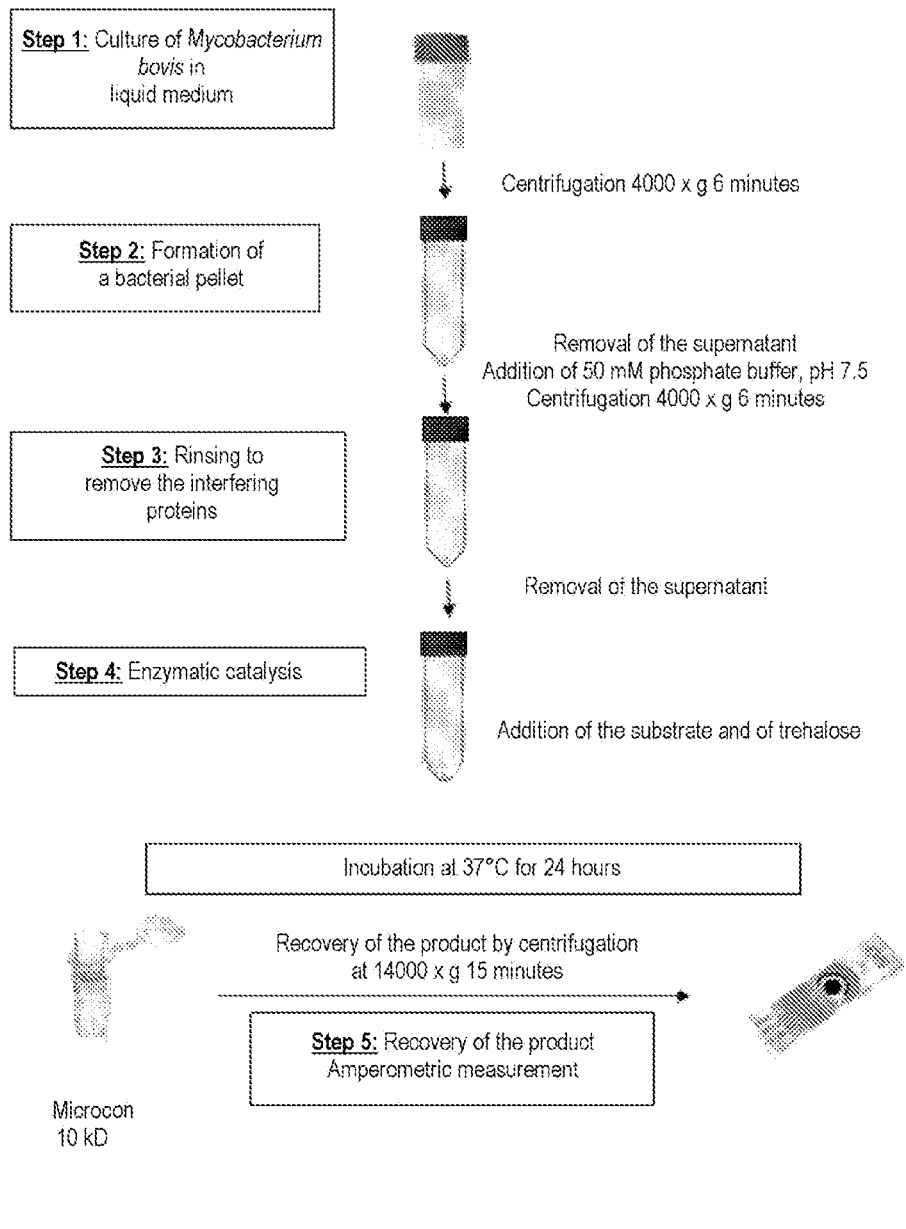
FIG. 6 represents the steps carried out during the detection of Ag85 in the bacterial pellet resulting from a culture of mycobacteria.
Figure 7:
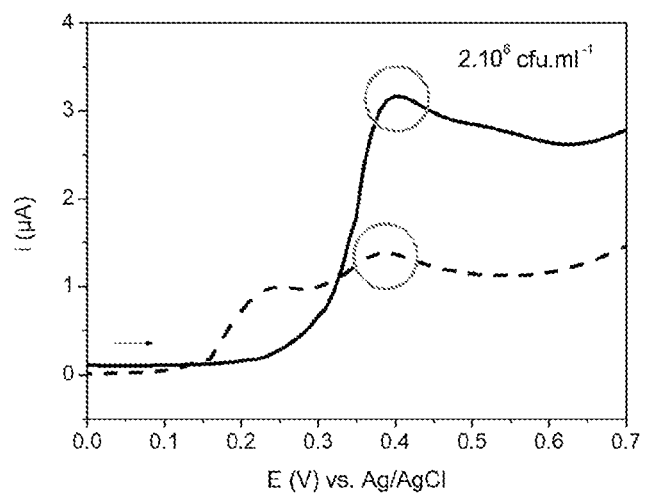
FIG. 7 represents the linear voltammograms (v=50 mV·s$^{-1}$) recorded by analyzing 10 ml volumes of a liquid culture of *M. bovis* BCG at $2 \times 10^6$ cfu·ml$^{-1}$ according to the protocols of FIGS. 4 and 6. The curve as a line --- corresponds to the response recorded for the supernatant and that as a continuous line was obtained for the analysis of the bacterial pellets.
Figure 8:
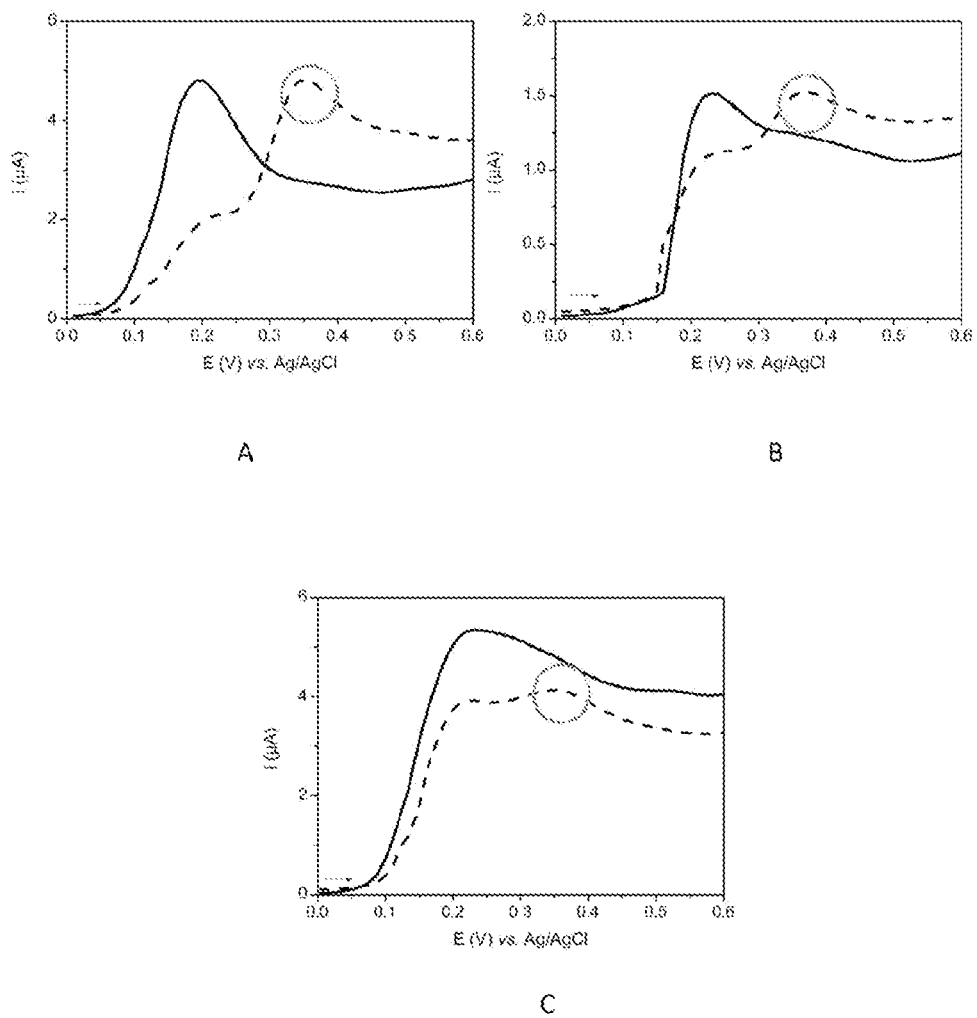
FIG. 8 represents the linear voltammograms (v=50 mV·s$^{-1}$) recorded by analyzing 1 ml of 7H9 culture medium+OADC (negative control; curve as a continuous line) containing (A) *M. intracellulare*, (B) *M. avium* and (C) *M. xenopi* at ~$10^6$ bacilli·ml$^{-1}$ (curved as a line ---) analyzed according to the protocol described in section 1.5.
Figure 9:
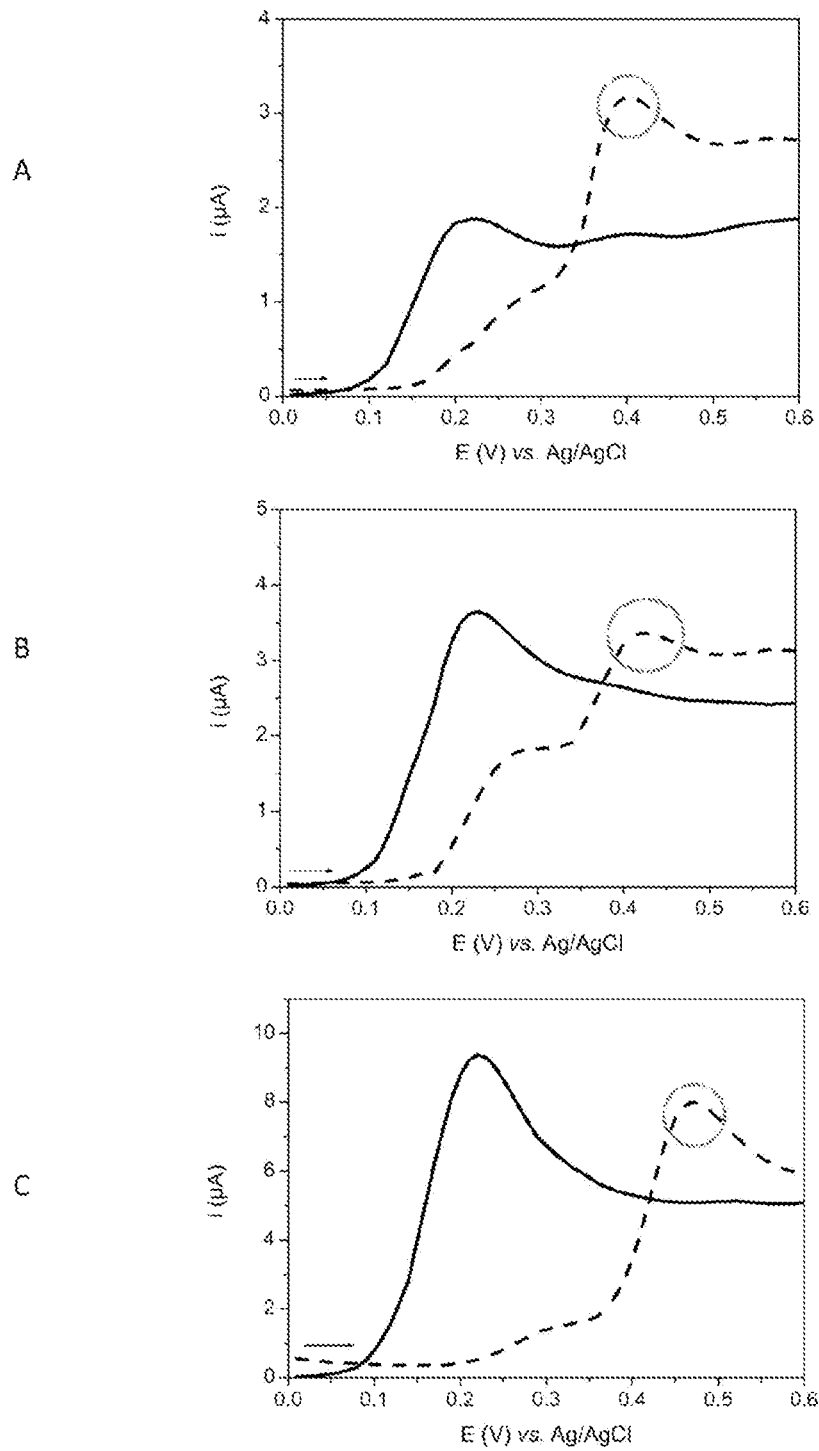
FIG. 9 represents the linear voltammograms (v=50 mV·s$^{-1}$) recorded for the qualitative analysis of a liquid culture of *M. tuberculosis* (A) culture supernatant, (B) bacterial pellet, and that (C) of isolated colonies of *M. tuberculosis* according to the protocol described in section 1.6. The curves as a line --- correspond to the *M. tuberculosis* response while the curves as a continuous line were obtained for the negative control.

In order to validate this hypothesis, Ag85 was also incubated in the presence of trehalose and of a mixture of p-AP-OG and p-AP-G. The comparison of the voltammograms (curve as a continuous line and dotted curve) of FIG. 3 confirms the identity of each peak shows that it is possible to envision electrochemical detection of Ag85 using p-AP-OG as substrate.

2.3. Electrochemical Detection of the Acyltransferase Activity of Ag85 in a Liquid Culture of *M. bovis* BCG For the purpose of applying the method for electrochemically detecting Ag85 in order to demonstrate the growth of mycobacteria in a liquid culture medium, the analysis of the supernatant of a culture of *M. bovis* BCG strain Pasteur (avirulent model vaccine strain of tuberculosis mycobacteria) and also that of the bacterial pellet were envisioned. The concentrations of substrate and of co-substrate, the enzymatic catalysis reaction time and also the need to include a filtration step before the electrochemical measurement were studied in a series of preliminary experiments.

2.3.1. Analysis of the Supernatant

1. It has been demonstrated that Ag85 is a major secretion product of *M. tuberculosis* in the replicative phase (Wiker and Harboe, Microbiol. Rev., 56(4): 648-661, 1992) [9]. The protocol represented schematically in FIG. 4 and described in section 1.4 was carried out in order to analyze 5 ml of a culture of *M. bovis* BCG containing $1.1\times10^{7}$ $cfu\cdot ml^{-1}$. A negative control (enriched 7H9 medium without bacteria) was analyzed in parallel according to the same protocol and the results are presented in FIG. 5. The voltammetric response of the negative control (curve as a continuous line) corresponds overall to the p-AP-OG oxidation peak located at around ~+0.25 V vs. Ag/AgCl, whereas that recorded for the culture supernatant (curve as a line ---) shows not only the p-AP-OG oxidation peak (with a lower intensity), but also the p-AP-G oxidation peak. The presence of the latter indicates the presence of Ag85 in the culture supernatant and therefore that of the mycobacteria in the culture analyzed.

2.3.2. Analysis of the Bacterial Pellet

Since Ag85 is also involved in the repair and construction of the wall of mycobacteria, the protocol represented schematically in FIG. 6 was carried out in order to analyze 10 ml of *M. bovis* BCG culture containing $2\times10^{6}$ $cfu\cdot ml^{-1}$. In parallel, the supernatant of this same culture was analyzed as previously.

The voltammogram (curve as a line ---) presented in FIG. 7 confirms the detection of the activity of Ag85 in the culture supernatant with the presence of the p-AP-OG and p-AP-G oxidation peaks. Furthermore, the voltammetric response recorded for the analysis of the bacterial pellet (curve as a continuous line) shows only the p-AP-G oxidation peak with a strong intensity. This result indicates that all of the p-AP-OG substrate has been converted into p-AP-G during the incubation step and thus suggests that the bacterial pellet contains a larger amount of Ag85 than the supernatant for a given culture volume. A supplementary study on the specificity of the method showed that the acyltransferases present in *Pseudomonas aeruginosa, Pseudomonas fluorescens, Pseudomonas monteilii, Staphylococcus aureus, Staphylococcus epidermidis, Streptococcus pyogenes, Rhodococcus corallinus, Achromobacter xylosoxidans, Citrobacter freundii, Enterobacter cloacae, Enterococcus faecalis, Enterococcus faecium, Klebsiella pneumoniae* and *Stenotrophomonas maltophilia* are capable of converting p-AP-OG into p-AP-G in the presence of trehalose.

Thus, the amperometric response of p-AP-G measured during the analysis of the bacterial pellet of *M. bovis* BCG probably results, on the one hand, from the acyltransferase activity of the Ag85 presence in the mycobacterial envelope and, on the other hand, from the acyltransferases contained in the mycobacteria.

2.4. Electrochemical Detection of Several Species of Mycobacteria in Liquid Cultures The proof of concept of the electrochemical detection of mycobacteria in the presence of p-AP-OG and trehalose was carried out for the analysis of several species of mycobacteria that can be handled in an L2 containment laboratory. The species selected are those frequently found in respiratory specimens: *M. intracellulare, M. avium* ssp. *avium* and *M. xenopi*. To do this, the protocol described in section 1.4 was carried out and the results obtained for the analysis of the bacterial pellets containing approximately $10^{6}$ bacilli are shown in FIG. 8. The obtaining of an oxidation peak specific for the product of hydrolysis of the substrate by Ag85 (p-AP-G) for the analysis of each species (curves as a line ---, E~+0.4 V vs. Ag/AgCl) confirms that it is possible to detect, with an electrochemical method, the presence of mycobacteria with p-AP-OG as substrate and trehalose as co-substrate. For each species, quantification thresholds of between $10^{3}$ and $10^{4}$ $bacteria\cdot ml^{-1}$ of culture were estimated.

2.5. Detection of *M. tuberculosis*

The electrochemical detection of *M. tuberculosis*, a class 3 microorganism responsible for human tuberculosis, was carried out by analyzing cultures of the H37Rv strain in 7H9 liquid medium and on 7H11 agar medium according to the procedures of section 1.6. In the case of liquid culture, the detection of Ag85 was envisioned in the bacterial pellet and also in the culture supernatant.

With an oxidation peak specific for the p-AP-OG hydrolysis product, the series of voltammograms presented in FIG. 9A confirms that the *M. tuberculosis* strain produces Ag85 in a large amount in the culture medium. These results confirm that it is possible to envision the detection of *M. tuberculosis* via the electrochemical measurement of the activity of Ag85 in the culture medium.

Moreover, the p-AP-G oxidation peaks recorded for the analysis of the bacterial cells (FIGS. 9B, 9C; curves as a line ---) indicate that the electrochemical method involving p-AP-OG as substrate and trehalose as acyl group accepter also makes it possible to detect *M. tuberculosis* in the form of bacterial pellets and of isolated colonies.

2.6. Extraction and Detection of *M. intracellulare* in a Respiratory Sample

In order to propose a method for direct (that is to say without prior culture) electrochemical detection of mycobacteria in samples of pulmonary origin (sputum, tracheal aspiration and bronchial aspiration products), specimens from nontuberculous patients were inoculated with a known amount of *M. intracellulare* and analyzed according to the protocol of section 1.7.

Since the commercially available fluidization-decontamination methods that are of use for the preparation of the samples—which combine N-acetylcysteine and sodium hydroxide—are not compatible with electrochemical detection (poorly defined signals), the development of a protocol for extracting the mycobacteria from specimens of pulmonary origin was envisioned. The method proposed involves a hexane-isopropanol mixture as extraction solvent. By precipitating the constituents of the respiratory specimen, isopropanol makes it possible to get rid of the viscous nature of the specimen, while the apolar solvent, which hexane is, selectively extracts the mycobacteria, the wall of which is very hydrophobic. Once recovered by filtration, the mycobacteria were incubated with the substrate/co-substrate mixture for the purpose of carrying out the electrochemical detection of the acyltransferase activity (Ag85 and other enzymes present in the mycobacterial cell).

Figure 10:
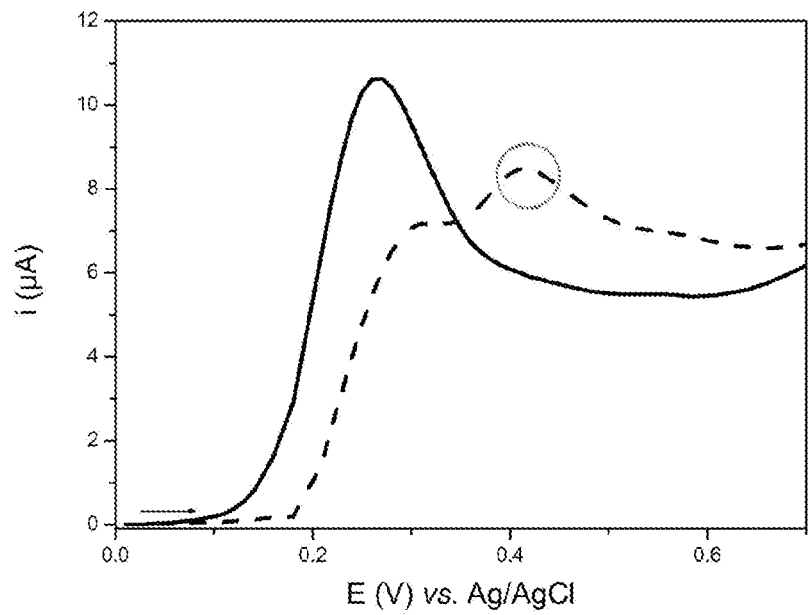
FIG. 10 represents the linear voltammograms (v=50 mV·s$^{-1}$) recorded after carrying out the protocol described in section 1.7 for the analysis of 1 ml of sputum inoculated with $10^6$ *M. intracellulare* bacilli (dashed curve) or not incubated (curve as continuous line).
Figure 11:
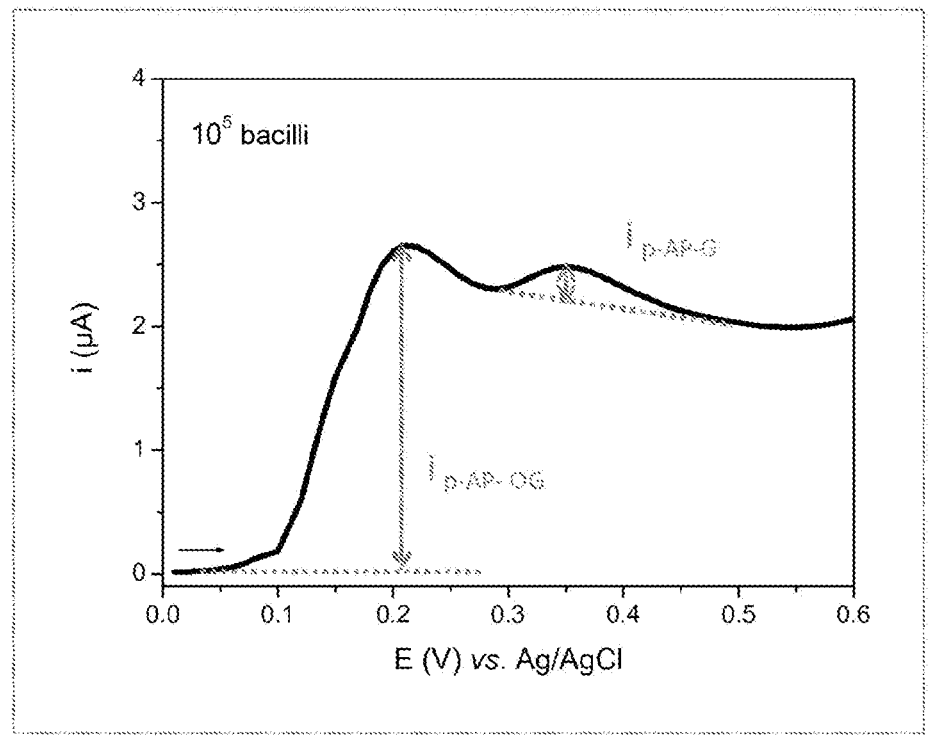
FIG. 11 represents the linear voltammogram (v=50 mV·s$^{-1}$) recorded by analyzing 1 ml of *M. intracellulare* culture at $10^5$ bacilli·ml-according to the protocol described in section 1.5. and also the values i p-AP-OG and i p-AP-G required for calculating the analytical response R.

The voltammograms presented in FIG. 10 show that it is possible to detect the mycobacteria by virtue of the electrochemical method in specimens of respiratory origin previously treated with a hexane-isopropanol mixture. Indeed, the oxidation peaks specific for the product of hydrolysis of p-AP-OG by Ag85 is obtained for the sputum inoculated with *M. intracellulare* (curve as a line ---, E~+0.4 V vs. Ag/AgCl) while no oxidation peak linked to the presence of p-AP-G was recorded for the non-inoculated sputum (curve as a continuous line).

2.7. Extraction and Detection of *M. bovis* BCG in a Soil Sample

In order to evaluate the impact of the volume of hexane on the extraction yield, sterile soil (5 g) was inoculated with the *M. bovis* BCG strain ($1.5 \times 10$ cfu per microcosm) and subjected to the extraction protocol described in section 1.8 using hexane volumes of 2 ml, 5 ml and 10 ml. The maximum extraction yield was obtained using a hexane volume of 10 ml. Under these conditions, 50% of the mycobacteria that were inoculated in the microcosms were extracted. This good extraction yield is linked to the high affinity between hexane and the hydrophobic membrane of the mycobacteria. Furthermore, hexane probably has a role in the destruction of the bonds (physisorption, chemisorption) which bring about adhesion of the mycobacteria with the soil particles.

The particular features of *M. bovis*, and in particular its very slow growth, generally require a step of decontaminating the extract before it is cultured, in order to remove the majority of the endogenous microorganisms from the environmental substrates while preserving the mycobacteria. Several protocols were evaluated and only the one combining extreme pH variations and incubation in the presence of sodium hypochloride was sufficiently effective for destroying all the interfering microbial flora of the soil co-extracted with the hexane at the same time as *M. bovis* BCG. By applying the extraction-decontamination protocol described in section 1.8 to sterile soil samples (5 g) inoculated with *M. bovis* BCG ($2.6\times10^6$ cfu per microcosm), a yield of 2.5±0.8% (n=4) was obtained. This result suggests that the decontamination is the limiting step in the approach since it removes 95% of the mycobacteria that were extracted with hexane. This step is, however, very useful, or even essential, for getting rid of the contaminating microorganisms which have a hydrophobic envelope similar to that of *M. bovis*, such as the various genera encountered in Actinobacteria.

Although the method for extraction-decontamination of the mycobacteria in soil of the invention makes it possible to recover only approximately 2.5% of the bacteria inoculated into sterile soil, this yield is much higher than that described in the literature for the analysis of naturally contaminated environmental samples with a magnetic immunocapture process (0.1%) (Sweeney et al., Lett. Appl Microbiol., 43(4): 364-369, 2006; Sweeney et al., Appl Environ Microbiol., 73(22): 7471-7473, 2007) [10, 11].

2.8. Quantitative Aspects of the Method

In order to take into account all of the random errors during the implementation of the protocols, p-AP-OG was chosen as an internal standard and the analytical response of the method was defined as the ratio of the intensity of the p-AP-G oxidation peak to the intensity of the p-AP-OG oxidation peak:

$$R = \frac{ip-AP-G}{ip-AP-OG}$$

The parameters $i_{p\text{-}AP\text{-}OG}$ and $i_{p\text{-}AP\text{-}G}$ have been defined on the voltammogram presented in FIG. 11.

As shown by the values of R collated in table 2 below, the electrochemical method proposed by the inventors made it possible to detect amounts of *M. intracellulare* of less than 100 bacilli·ml$^{-1}$. This result makes it possible to envision applications of the method for the analysis of actual samples, after extraction of mycobacteria, without having recourse to a prior culture step.

TABLE 2

Standardized analytical responses R ($R_0$ corresponds to the analytical response registered for the culture medium without bacteria) calculated from the voltammograms recorded for the analysis of *M. intracellulare* at $10^2$, $10^3$, $10^4$, $10^5$ and $10^6$ *bacilli* · ml$^{-1}$ according to the protocol described in section 1.4.

| *M. intracellulare* (*bacillus* · ml$^{-1}$) | $R/R_0$ |
|---|---|
| 0 | 1 |
| $10^2$ | 2.9 |
| $10^3$ | 4.5 |
| $10^4$ | 7.4 |
| $10^5$ | 12.2 |
| $10^6$ | 40 |

Finally, a first repeatability study was carried out for the analysis of the pellet of a culture of *M. intracellulare* containing $5\times10^6$ bacilli·ml$^{-1}$. A coefficient of variation of 94% was calculated for 5 repetitions.

2.9. Application of the Method of Electrochemical Detection of the Invention to the Monitoring of *Mycobacterium tuberculosis* H37Rv Growth in Liquid Medium 2.9.1. Comparison of the Time to Positivity of a Liquid Culture of *Mycobacterium tuberculosis* H37Rv with the BD BACTEC™ MGIT™ Automated Device To do this, three volumes of medium (volumes, A, B and C) were prepared for testing the detection method described in the invention (Table 3).

TABLE 3

Volumes of the various reagents used to prepare the culture media

| Reagents | BACTEC ™ | Electrochemical detection Volume A | Volume B | Volume C |
|---|---|---|---|---|
| BD BACTEC ™ MGIT ™ medium | 7 ml | 3.5 ml | 2 ml | 1 ml |
| Growth supplement and BBL MGIT ™ PANTA | 0.8 ml | 0.4 ml | 230 µl | 115 µl |
| p-AP-OG $2\times10^{-2}$M | | 100 µl | 57 µl | 29 µl |
| Trehalose $5\times10^{-1}$M | | 100 µl | 57 µl | 29 µl |
| Final volume | 7.8 ml | 4.1 ml | 2.344 ml | 1.173 ml |

An *M. tuberculosis* bacterial suspension was prepared then diluted twice to one tenth in 7H9 culture medium (samples −1 and −2). These diluted suspensions were used to inoculate the various tubes.

The tubes incubated in the BACTEC™ automated device were subjected to an automatic measurement of the fluorescence once an hour. The time to positivity was expressed in days.

The tubes were analyzed daily by the method of the invention, by taking a volume of 30 μl of the culture and depositing it at the surface of a screen-printed sensor without prior treatment. The measurements were carried out by linear voltammetry and the positivity of the sample corresponds to the appearance of a p-AP-G oxidation peak at around ~+0.50 V vs. Ag/AgCl.

Since the electrochemical measurements were not carried out continuously (once a day in the best of cases), there is for the moment an uncertainty about the exact moment at which the positivity appears, hence the expression of the results in the form of ≤x days.

TABLE 4

Times to positivity obtained with the BACTEC ™ automated device and with the electrochemical method during the incubation of control tubes and of tubes inoculated with *M. tuberculosis* H37Rv (1 to 2 repetitions per sample)

| Samples | BACTEC ™ (time in days) | Electrochemical detection (time in days) | | |
|---|---|---|---|---|
| | | Volume A | Volume B | Volume C |
| Control 1 | Negative | Negative | Negative | Negative |
| Control 2 | Negative | Negative | | |
| −2 | 6.09 | ≤7 | ≤7 | ≤4 |
| −2 | 6.09 | ≤7 | ≤7 | ≤3 |
| −1 | 4.2 | ≤4 | ≤3 | ≤2 |
| −1 | 4.21 | ≤4 | ≤3 | ≤2 |

The results of table 4 indicate that the electrochemical method made it possible to monitor the culture of *M. tuberculosis* in lower volumes (volume C) than the BACTEC™ method, and thus to reduce the time to positivity of the sample (≤2 days instead of 4 days for the dilution −1 and ≤3-4 days instead of 6 days for the dilution −2).

2.9.2. Comparison of the Time to Positivity of Four Respiratory Samples Inoculated or not Inoculated with *M. tuberculosis* H37Rv, after Fluidization-Decontamination with the BD BACTEC™ MGIT™ Automated Device Four respiratory samples were supplied by the CHU Dijon (samples 1 and 2: fibroscopy, sample 3: bronchoalveolar lavage and sample 4: sputum). For each sample, a 3 ml aliquot was contaminated with 500 μl of *M. tuberculosis* H37Rv suspension; a second aliquot, which was not contaminated, served as a control. After a fluidization-decontamination step (Biocentric NacPac kit), each pellet was resuspended in 1.1 ml of culture medium. Two volumes of 500 μl of the previous solution are then respectively introduced into a BACTEC™ tube and a Falcon tube containing the medium A (table 3).

The tubes incubated in the BACTEC™ automated device were subjected to an automatic measurement of the fluorescence once an hour. The time to positivity was expressed in days.

The cultures carried out in the volumes of medium A (table 3) were incubated at 37° C. and analyzed with the electrochemical method of the invention. The electrochemical measurements and the interpretation thereof were carried out as in section 2.9.1. above.

TABLE 5

Time to positivity of four respiratory samples that were contaminated or not inoculated (control) in MGIT tubes obtained with the electrochemical method and the BACTEC automated device

| Respiratory samples | BACTEC ™ (time in days) | | Electrochemical detection (time in days) | |
|---|---|---|---|---|
| | Control | Inoculated | Control | Inoculated |
| Sample 1 | — | 9.15 | — | ≤7 |
| Sample 2 | — | 4.16 | — | ≤5 |
| Sample 3 | — | 5.07 | — | ≤5 |
| Sample 4 | — | 5.20 | — | ≤5 |

The results collated in table 5 show that the electrochemical method was as effective as BACTEC™ for the detection in liquid culture of respiratory samples artificially contaminated with *M. tuberculosis*.

Finally, by combining the results of tables 4 and 5, the electrochemical method of the invention is capable of demonstrating more rapidly the growth of *M. tuberculosis* in a liquid culture (~two times less time) and thus its presence in a respiratory sample.

LIST OF REFERENCES

1. Phunpae et al., Diagn. Microbiol. Infect. Dis., 78(3): 242-248, 2014
2. Kashyap et al., BMC infectious diseases, 7:74, 2007
3. Kashyap et al., Clin Diagn Lab Immunol., 12(6):752-758, 2005
4. Elamin et al., J. Microbiol. Methods, 79(3): 672-678, 2002
5. Boucau et al., Analytical Biochem., 385: 120-127, 2009
6. Favrot et al., J. Biol. Chem., 289(36): 25031-25040, 2014
7. International application WO 2011/030160
8. Patent application CN102087283
9. Wiker and Harboe, Microbiol. Rev., 56(4): 648-661, 1992
10. Sweeney et al., Lett. Appl. Microbiol., 43(4):364-369, 2006
11. Sweeney et al., Appl. Environ. Microbiol., 73(22): 7471-7473, 2007.

The invention claimed is:

1. A process for electrochemical detection of mycobacteria in a biological sample, said process comprising the steps of:
   a) providing p-aminophenyl-6-O-ocatanoyl-β-glucopyranoside as a substrate for acyltransferase Antigen 85 (Ag85) and a sugar selected from trehalose and D-glucose wherein said sugar is a cofactor for the acyltransferase;
   b) bringing said biological sample into contact with said substrate and cofactor; and
   c) electrochemically detecting the product resulting from the catalytic activity of said acyltransferase.

2. The process as claimed in claim 1, wherein the biological sample is selected from bacterial cultures, biological specimens of human or animal origin, and environmental samples.

3. The process as claimed in claim 1, wherein the electrochemical detection step c) is carried out by an amperometric sensor.

4. The process as claimed in claim 1, wherein said mycobacteria has been isolated from the biological sample comprising the steps of:

A) placing said biological sample in solution;

B) contacting the solution obtained in step A) with an apolar solvent;

C) recovering the mycobacteria by membrane filtration or centrifugation of the solution resulting from step B); and D) recovering the mycobacteria from the resultant filtrate or from the resultant centrifugation pellet obtained at the end of step C).

5. The process as claimed in claim 4, further comprising a step of A') decontaminating the biological sample placed in solution at the end of step A) and before step B), and/or a step C') of decontaminating the membrane filter at the end of step C) and before step D).

6. The process as claimed in claim 5, wherein step C') is carried out by the addition of one or more of acidic solutions, basic solutions, sodium hypochlorite, or at least one disinfecting compound.

7. The process as claimed in claim 5, further comprising a step C'') of rinsing the membrane filter at the end of step C') and before step D).

8. The process as claimed in claim 7, wherein the rinsing step C'') is carried out with a phosphate buffer.

9. A kit for carrying out the process for electrochemical detection of mycobacteria in a biological sample as defined in claim 1, comprising:
   i) a device and the reagents for collecting and preparing the biological sample to be tested;
   ii) a device comprising p-aminophyenyl-6-O-ocatanoyl-β-glucopyranoside as a substrate of Ag85 and a sugar selected from trehalose and D-glucose wherein said sugar is a cofactor for Ag85; and
   iii) a device for the electrochemical detection.

10. The kit as claimed in claim 9, wherein the device for the electrochemical detection is an amperometric sensor.

11. The kit as claimed in claim 10, wherein the amperometric sensor is a screen printed sensor.

* * * * *